(12) United States Patent
Da Lúz Moreira et al.

(10) Patent No.: US 8,383,168 B2
(45) Date of Patent: Feb. 26, 2013

(54) ANTIOXIDANT COMPLEX, COSMETIC AND PHARMACEUTICAL COMPOSITIONS CONTAINING SAID COMPLEX AND USE OF SAID COMPLEX

(75) Inventors: Patricia Da Lúz Moreira, São Paulo (BR); Kelen Fabiola Arroteia, Campinas (BR); Cintia Rosa Ferrari, Carapicuiba (BR); Adriano Tadeu Siqueira Jorge, Guarulhos (BR); Juliana Carvalhães Lago, Campinas (BR); Jean Luc Gesztesi, São Paulo (BR); Philip Leite Ribeiro, legal representative, São Paulo (BR)

(73) Assignee: Natura Cosmeticos S.A., Itapecerica da Serra-SP (BR)

( * ) Notice: Subject to any disclaimer, the term of this patent is extended or adjusted under 35 U.S.C. 154(b) by 0 days.

(21) Appl. No.: 13/126,352

(22) PCT Filed: Oct. 30, 2009

(86) PCT No.: PCT/BR2009/000359
§ 371 (c)(1),
(2), (4) Date: Feb. 28, 2012

(87) PCT Pub. No.: WO2010/048686
PCT Pub. Date: May 6, 2010

(65) Prior Publication Data
US 2012/0171308 A1    Jul. 5, 2012

(30) Foreign Application Priority Data
Oct. 30, 2008  (FR) ..................................... 08 57394

(51) Int. Cl.
*A01N 65/00*    (2009.01)
(52) U.S. Cl. ..................................................... 424/725
(58) Field of Classification Search .................. None
See application file for complete search history.

(56) References Cited

U.S. PATENT DOCUMENTS

| | | |
|---|---|---|
| 2004/0023894 A1 | 2/2004 | Hasler-Nguyen et al. |
| 2004/0161435 A1 | 8/2004 | Gupta |
| 2004/0208902 A1 | 10/2004 | Gupta |
| 2005/0048143 A1 | 3/2005 | McAnalley et al. |
| 2006/0216264 A1 | 9/2006 | Maguire |
| 2006/0251608 A1 | 11/2006 | Wachsberg et al. |
| 2007/0014876 A1 | 1/2007 | Shapira et al. |
| 2007/0116838 A1 | 5/2007 | Prakash et al. |
| 2008/0089941 A1 | 4/2008 | Mower |

FOREIGN PATENT DOCUMENTS

| | | |
|---|---|---|
| FR | 2 841 102 A | 12/2003 |
| FR | 2 873 026 A | 1/2006 |
| JP | 2 264 720 A | 10/1990 |
| KR | 2001 0002411 A | 1/2001 |
| KR | 2005 0007718 A | 1/2005 |
| WO | WO 01/17484 A | 3/2001 |
| WO | WO 01/93816 A | 12/2001 |
| WO | WO 02/100329 A | 12/2002 |
| WO | WO 2006/117465 A | 11/2006 |
| WO | WO 2007/140022 A | 12/2007 |
| WO | WO 2008/027063 A | 3/2008 |

OTHER PUBLICATIONS

International Search Report and Written Opinion for International Application No. PCT/BR2009/000359, flied Oct. 30, 2009.
International Preliminary Report on Patentability for International Application No. PCT/BR2009/000359, filed Oct. 30, 2009.

*Primary Examiner* — Michael Meller
(74) *Attorney, Agent, or Firm* — Alston & Bird LLP

(57) ABSTRACT

The present application describes an antioxidant complex having a synergistic effect between its ingredients. Said mixture comprises: a) vitamin E and/or derivatives thereof; b) green tea extract and/or derivatives thereof; and c) cacao extract. Examples of cosmetic and pharmaceutical compositions comprising said antioxidant complex and a physiologically acceptable carrier are also described. The antioxidant complex of the present invention, as well as the aforementioned compositions, aid in preventing and protecting against cell and skin damages resulting from the action of free radicals, and also provide DNA, protein and cell membrane protection.

15 Claims, 9 Drawing Sheets

Formation of protein Hydroperoxides (BSAOOH)

ANTIOXIDANT COMPLEX, COSMETIC AND PHARMACEUTICAL COMPOSITIONS CONTAINING SAID COMPLEX AND USE OF SAID COMPLEX

The present invention relates to an antioxidant complex to help prevent and protect against cell and skin damage resulting from the action of free radicals.

The present invention further relates to cosmetic and pharmaceutical compositions comprising said antioxidant complex.

DESCRIPTION OF THE PRIOR ART

The process for producing energy in cells takes place in specialized cytoplasmatic organelles, the mitochondria. This process is in fact a gradual redox reaction, in which glucose molecules ($C_6H_{12}O_6$) oxidize, originating carbon dioxide molecules ($CO_2$), and oxygen molecules are reduced, originating water molecules ($H_2O$).

The complete oxidation of oxygen into water occurs in steps, and highly energetic intermediates are formed.

These intermediates are referred to as reactive oxygen species (ROS) and their main characteristic is their high reactivity. Most of these molecules can also be classified as free radicals, which are molecules capable of existing independently and which have one or more unpaired electrons.

This characteristic is the main factor responsible for the reactivity of these radicals, since because they have unpaired electrons, these molecules are capable of taking these electrons from other molecules, oxidizing them.

The main reactive oxygen species generated in the cells are the following:

Superoxide Radical ($O^{2-}$): formed right after the first reduction of oxygen, it occurs in almost all eukaryotic cells and plays an important role in secondary biological damages.

Hydroperoxyl Radical ($HO^{2-}$): protonated form of the superoxide anion, it is more reactive than the first one; however, it is not often present in physiological pH.

Hydroxyl Radical ($OH^-$): This ROS is more reactive in biological systems and is formed from hydrogen peroxide —$H_2O_2$, which is not a free radical but is highly toxic for cells, in addition to being important in oxidation reactions, since it is the substrate which originates the hydroxyl radical. It is highly capable of oxidizing cellular macromolecules such as membrane lipids, proteins and DNA.

Oxygen singlet ($1O_2$): excited form of molecular oxygen—without unpaired electrons—formed in sensitization reactions.

Since these molecules are highly reactive and harmful to cells, but are formed in large amounts in the cellular respiration process for the production of energy, the organism has its own defense mechanisms to reduce the amount of these radicals available. The enzymatic defense system comprises the enzymes which catalyze the reduction of oxygen and its intermediates: SOD (superoxide dismutase), catalase, glutathione peroxidase, in addition to peroxiredoxins. The nonenzymatic system basically comprises the ascorbic acid (vitamin C) and tocopherol (vitamin E).

Even though the organism has its own defense system, in many cases the level of free radicals formed may exceed its natural neutralization capacity, resulting in an excess of free radicals referred to as oxidative stress.

In the skin this state may result from exposure to UV radiation, from inflammatory processes or from the aging process, when the antioxidant defenses decrease and free radical generation increases.

Lipid Oxidation (lipoperoxidation): Lipid oxidation or lipoperoxidation is a chain reaction divided into three phases: initiation, propagation and termination. In the initiation phase, a free radical takes an electron from a lipid, oxidizing it and transforming it into a lipid radical. In the propagation phase, this lipid radical, in the presence of oxygen, generates the peroxyl radical, which originates the lipid hydroperoxides and finally the alkoxyl radicals. In this phase, the intermediate radicals formed attack new lipid molecules, resulting in a very fast propagation of the damages. The lipid peroxidation reaction ends when a radical interacts with another, forming the cyclic peroxides. This reaction may cause the death of the cell, since the cell membrane is responsible for selectivity in cell permeability.

DNA Oxidation: DNA bases may also be oxidized by free radical attack. These modifications are typically repaired by specific cell mechanisms; however, depending on the extent of the damage and of the molecular modifications, they may evolve into mutations and contribute to the development of skin cancer, for example.

Protein Oxidation: Proteins are also targets of free radical oxidative attacks. In this case, the amino acids are modified, which causes structural alterations (breakdown of the polypeptide chain and modification of the amino acid side chain) and often functional alterations of these proteins. These alterations convert the proteins into derivatives which are much more sensitive to proteolytic degradation.

As widely known by those skilled in the art, a large variety of combinations of antioxidant ingredients is available for cosmetic and/or pharmaceutical use.

Korean document KR 20010002411 describes a cosmetic composition having antioxidant effects, based on the combination of cacao extract, green tea leaf extract and coffee bean extract, which composition is effective in preserving articles containing vitamin C, in addition to causing very low irritation to the skin of the user.

Japanese document JP 2264720 discloses a suppressing preparation which is effective in controlling and inhibiting the damages caused by the formation of active oxygen in the cells. Said preparation is based on a mixture comprising a "substance"+vitamin, both resistant to oxidation. Powdered tea (not specified) and cocoa powder are mentioned as options of oxide-resistant "substances".

US document 2005/048143 relates to an antioxidant composition comprising a flavonoid, such as quercetin, in combination with at least a mixture of vitamin E derivatives. Additionally, said composition may comprise green tea extract.

US document 2007/116838 describes a functional sweetener composition comprising among its ingredients at least one antioxidant which may be selected from a specified group composed of: cacao extract, green tea extract, tocopherol-derived compounds, xanthine derivatives, and resveratrol, among others. This document does not describe the antioxidants or their combinations in detail.

US document 2008/089941 discloses a composition for delivery of partially hydrolyzed and/or sulfonated fucoidan, comprising among its ingredients an antioxidant selected from a specified group composed of vitamin E, rutin, cacao and resveratrol.

US document 2004/208902 describes a cosmetic and/or pharmaceutical composition comprising among its ingredients a zeolite and at least an active ingredient which promotes topical benefits and which requires a controlled-release system. This composition comprises antioxidants which may be selected from a specified group composed of vitamin E, tocotrienol, green tea extract, polyphenols, and rosemary acid, among others.

US document 2004/023894 relates to an antioxidant composition based on the combination of [delta] tocols, such as delta-tocopherol and polyphenols from *Citrus* sp, preferably. This composition is useful for treating or preventing disorders relating to free radical generation.

US document 2004/161435 describes a cosmetic mask composition for treating cellulite and reducing body fat, among others. The mask composition comprises among its ingredients at least an agent which promotes topical benefits, such as, for example, an antioxidant agent.

US document 2007/014876 relates to a composition for potentiating antioxidant activities, comprising at least one antiacid component in a dose sufficient to elevate the pH in the stomach; at least one antioxidant component which decreases free radical generation, among others.

US document 2006/251608 describes a method of treating skin aging, wrinkles and other signs of damaged skin by applying a topical formulation and using an oral formulation comprising one or more antioxidants.

Brazilian document PI 0000018-3 discloses a skin whitening mixture based on the combination of bearberry and an antioxidant which may be selected from: tetrahydrocurcumin, preferably, tocopherol and rosemary extract, among others.

Based on the information above, it can be observed that most cosmetic products used during sun exposure or for treating and protecting against skin aging contain antioxidant substances in their compositions to aid in combating free radical excess.

From the description of the present invention provided below, it can be concluded that no prior-art teaching describes or suggests an antioxidant complex having a synergistic combination of three active ingredients, namely, vitamin E and/or derivatives thereof; green tea extract and/or derivatives thereof; and cacao extract containing a mixture of xanthines+catechins, at concentration ranges which potentiate the antioxidant effect, nor does any said prior-art teaching provide advantages with respect to financial costs, to the stability of the cosmetic composition and to the fairly high antioxidant potential, which results in improved skin protection against cell and skin damage.

Thus, it is concluded that antioxidant complexes having a synergistic combination of at least 3 of its active ingredients, as well as the cosmetic and/or dermatological use thereof, have not been developed yet.

OBJECTS OF THE INVENTION

The object of the present invention is to provide a complex having highly effective antioxidant activity, which may be used in isolation or applied in cosmetic and/or pharmaceutical compositions so as to provide them with functional benefits. This antioxidant complex provides protection against lipoperoxidation, DNA oxidation and protein oxidation.

A further object of this invention is to provide a cosmetic composition and a pharmaceutical composition comprising said antioxidant complex.

BRIEF DESCRIPTION OF THE INVENTION

The subject matter of the invention is an antioxidant complex having a synergistic effect between the following ingredients: vitamin E and/or derivatives thereof; green tea extract (*Camellia sinensis*) and/or derivatives thereof; and cacao extract (*Theobroma cacao*) and/or derivatives thereof. Said antioxidant complex, whether or not applied to cosmetic and/or pharmaceutical compositions, provides the functional benefits of combating the damages caused to the cells, and consequently to the skin, due to oxidative stress. Some of the aforementioned damages are listed below:

lipoperoxidation,
DNA oxidation, and
protein oxidation.

A further subject matter of this invention consists of a cosmetic and pharmaceutical composition comprising from 0.003% to 3.000% by weight of the antioxidant complex, based on the total weight of the composition, and a pharmaceutically acceptable carrier. Preferably, said compositions comprise:

an antioxidant complex composed of:
a) from 1 µg/ml to 20000 µg/ml of Vitamin E;
b) from 10 µg/ml to 1000 µg/ml of green tea extract;
c) from 10 µg/ml to 1000 µg/ml of cacao extract, based on the total weight of the antioxidant complex and
a physiologically acceptable carrier.

DETAILED DESCRIPTION OF THE INVENTION

Figure 1:
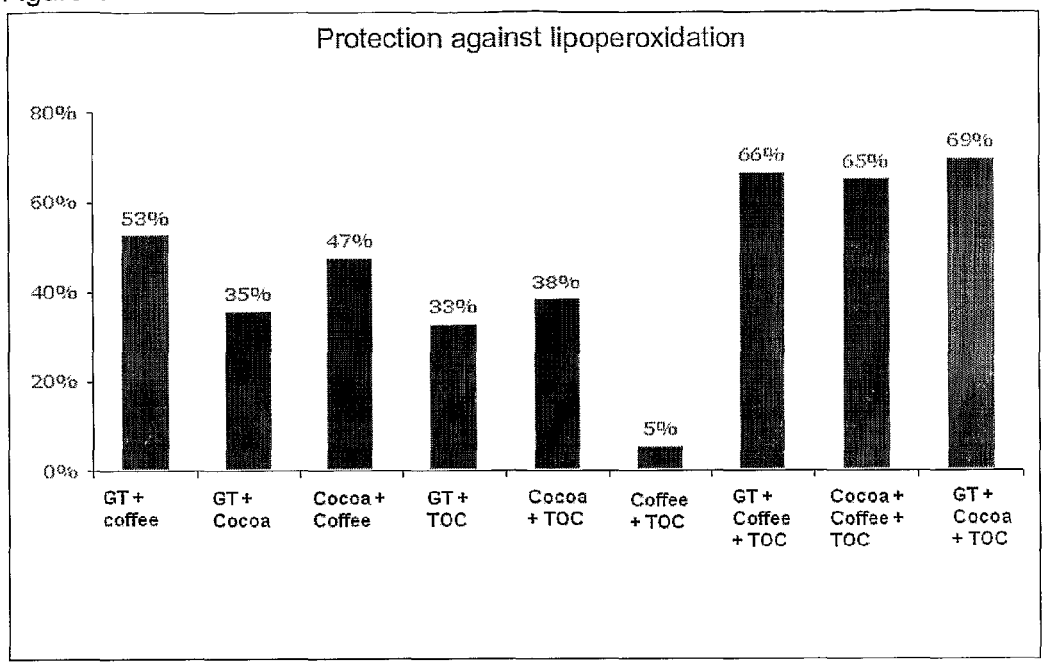
FIG. 1 illustrates a graph showing the levels of protection against lipoperoxidation of the components of the mixtures combined 2 by 2 vs. the mixture of the three.

The present invention describes an antioxidant complex comprising at least Vitamin E, green tea extract and cacao extract. This complex aids in preventing and protecting against cell and skin damages resulting from the action of free radicals.

An antioxidant complex is defined herein as a composition comprising at least 3 components which have antioxidant potential and which, when combined, exhibit an unexpected synergistic effect, achieving a much higher antioxidant potential. Additionally, said antioxidant complex provides protection against the action of free radicals, DNA oxidation and protein oxidation.

The present invention further describes topical cosmetic and pharmaceutical compositions for treating and/or protecting the skin, formed by a combination of water-soluble and liposoluble antioxidant agents in the same complex, which enables a proper activity in both hydrophilic and lipophilic biological media.

The new antioxidant complex according to the present invention can be used in formulations of products for exposition to the sun as well as in anti-aging products. In addition, it can be used in specific products wherein the antioxidant protection is important (for example, anti-pollution product).

The main examples of products which can be prepared with the antioxidant complex of the present invention or with cosmetic and pharmaceutical compositions comprising said complex are the following:

Moisturizing body milk;
Moisturizing facial milk;
Moisturizing body lotion;
Moisturizing facial lotion;
Gels;
Products for the scalp;
Sunblocks or sunscreens for adults or children, whether or not intended for concomitant use with the practice of sports;
Body or facial moisturizers;
Body or facial anti-spot/aging products;
Body or facial firming products;
Self-tanning products;
Insect repellant products;
Skin brightening body or facial moisturizers;
Topical pharmaceutical preparations;
Body or facial cosmetic preparations for children;
Cosmetic preparations for use in specific areas, such as the periocular region, the lip contour and the lips, anti-blemishes, anti-dark circles, among others;
Anti-acne products;
Products for skin lightening;
Pharmaceutical compositions for treating specific dermatoses;
Lipsticks and waxy bases;
Blushers and tinted bases;
Facial powders;
Any makeup product for use in the area of the eyes.

The antioxidant complex of the present invention, incorporated into cosmetic or pharmaceutical compositions, exhibits a number of advantages and features which are desirable in a cosmetic or pharmaceutical product for the skin, some of which are listed below:

1. It provides increased skin protection, combating the action of free radicals resulting from ultraviolet radiation, which has in its spectrum wavelength ranges known to promote the formation of these species. It is thus useful for formulating sunscreens and post-sun products which protect the skin more effectively against damages caused by sun exposure;

2. It provides increased skin protection against the formation of free radicals resulting from the exposure to different polluting agents, amongst which cigarette smoke. It is thus useful for preparing product formulations which protect the skin against these agents;

3. It aids in maintaining the balance between the formation of, and the combat to, free radicals, minimizing the oxidative stress situation, which is very common in the natural aging process of the skin. Thus, it is useful for preparing more effective anti-spot/aging formulations;

4. It does not require refrigerated storage;

5. The products comprising the antioxidant complex of the present invention are free from organoleptic alterations, unlike some prior-art products, such as:

a. Products containing vitamin C or derivatives thereof usually exhibit significant changes in aspect, color and odor.

6. The antioxidant complex of the present invention can be incorporated into various galenic forms, such as: aqueous gels, alcoholic gels, ointments, unguents, aqueous or alcoholic fluids, water in oil emulsions, oil in water emulsions, water in silicone emulsions, sold under the names of cream gels, creams, lotions, waxy bases, tinted powders, tinted bases, among other possibilities of galenic forms, maintaining the stability of these compositions;

7. The antioxidant complex, whether or not combined with sunscreen, protects against the oxidative damages to DNA resulting from the increase in the formation of free radicals in situations such as sun exposure and skin aging;

8. The antioxidant complex of the present invention also protects against protein oxidation;

9. The antioxidant complex of the present invention also protects against lipid membrane oxidation;

10. The antioxidant complex of the present invention also exhibits a highly effective activity in neutralizing free radicals;

11. The antioxidant complex of the present invention can be added to formulations with photoprotective agents containing physical and/or chemical sunscreens in combination;

12. The antioxidant complex of the present invention comprises a combination of water-soluble and liposoluble antioxidant agents. Thus, it is suitable for use both in hydrophilic and lipophilic biological media, unlike most prior-art products of this type.

Antioxidant Complex

The antioxidant complex of the present invention exhibits a synergistic effect and comprises:

a) from 1 μg/ml to 20000 μg/ml of Vitamin E;
b) from 10 μg/ml to 1000 μg/ml of green tea extract;
c) from 10 μg/ml to 1000 μg/ml of cacao extract,
all the amounts are based on the total weight of the antioxidant complex.

In addition to these components, the antioxidant complex may further comprise optional antioxidant agents.

In preferred embodiments, the antioxidant complex of the present invention exhibits a synergistic effect and comprises:

a) from 10 μg/ml to 200 μg/ml of Vitamin E;
b) from 10 μg/ml to 100 μg/ml of green tea extract;
c) from 10 μg/ml to 100 μg/ml of cacao extract,
all the amounts are based on the total weight of the antioxidant complex.

In a preferred embodiment, the antioxidant complex of the present invention exhibits a synergistic effect and comprises:

a) 10 μg/ml of tocopherol acetate;
b) 10 μg/ml of green tea extract comprising a mixture of polyphenols, amongst which catechins; and
c) 10 μg/ml of *Theobroma cacao* extract rich in catechins and xanthines,
all the amounts are based on the total weight of the antioxidant complex.

On the other hand, the cosmetic and pharmaceutical compositions comprising the antioxidant complex of the present invention may further contain various components such as photoprotective agents (sunscreens) and other agents having specific functions required for each composition intended for each situation, such as sequestering agents, thickening agents, pH adjusting agents, preservative agents, humectants, emollients, dyes, oiliness adsorbing agents, active ingredients such as anti-aging agents, among others.

The components present in the antioxidant complex of the present invention will be described in more detail below:

Vitamin E

It can be added to cosmetic formations in its free from (tocopherol) or in its esterified form (tocopherol acetate).

The first form has a better performance as antioxidant, but because it is highly unstable when exposed to light and heat, it is often substituted with the second form, which exhibits better stability.

Tocopherol is an active, lipophilic antioxidant which has high affinity for cell membranes and aids in protecting against lipoperoxidation. The tocopherol acetate form, which is more stable and is usually applied to formulations, needs to be hydrolyzed by skin-specific enzymes (esterases).

Vitamin E acts as an antioxidant (neutralizing the action of free radicals), exhibits anti-inflammatory activity and reduces the amount of cells damaged by UV radiation.

In the preferred embodiments, vitamin E, preferably a tocopherol derivative, more preferably tocopheryl acetate, is added in an amount varying from 1 μg/ml to 20000 μg/ml, preferably from 10 μg/ml to 200 μg/ml, based on the total weight of the antioxidant complex.

Green Tea

Dry Green Tea Extract (*Camellia sinensis*): This antioxidant active ingredient is composed of polyphenols (mostly catechins). It is a hydrophilic active ingredient and comprises catechins.

The green tea extract acts as an antioxidant (neutralizing the action of free radicals), in addition to having anti-inflammatory and immunoprotective activity.

In the preferred embodiments, green tea extract, preferably green tea extract (*Camellia sinensis*) composed mostly of catechins, is added in an amount varying from 10 μg/ml to 1000 μg/ml, preferably from 10 μg/ml to 100 μg/ml by weight, based on the total weight of antioxidant complex.

Cacao Extract

Dry cacao extract (*Theobroma cacao*): Active ingredient having a high content of catechins and xanthines. It is a hydrophilic active ingredient, also known to have antioxidant activity. Preferably, the cacao extract used is rich in methylxanthines, such as caffeine and theobromine, and in chatechins/epicatechins.

Cacao beans have a high content of active chemical substances, amongst which polyphenols, catechins, xanthines, etc. These substances confer important therapeutic characteristics to this plant, such as: antioxidant activity, increased lipolysis, cell protection, etc. Because they contain these substances and exhibit these activities, cacao extracts may be used in products for skin treatment, sun protection, against cellulite, among others.

In a preferred mode, the cacao extract used has a high content of catechin and is obtained from nonfermented beans. In order to obtain this kind of extract, the cacao bean needs to be worked to inactivate the enzyme that causes catechin degradation, which can be done in one of the following manners:

the beans are heated at a high temperature, then dried;

the fruit is broken after 7 days from the day of the harvest, followed directly by drying, without going through the conventional fermentation process;

the fruit is broken on the day of the harvest, followed directly by drying, without going through the conventional fermentation process; or the fruits are gathered, broken, washed with running water to remove the pulp, then dried.

This last process has proven to be more advantageous for obtaining extract that is rich in the compounds responsible for the activity expected for the present invention.

In the preferred embodiments of the present invention, cacao extract, preferably cacao extract (*Theobroma cacao*) composed mostly of catechins and xanthines, is added in an amount varying from 10 μg/ml to 1000 μg/ml, preferably from 10 μg/ml to 100 μg/ml by weight, based on the total weight of antioxidant complex.

Optional Antioxidant Agent

Other optional antioxidant agents may also be added to the antioxidant complex.

Some examples of the compounds having antioxidant properties which may be added to the compositions of the present invention are: lipophilic substances such as butylated hydroxytoluene (BHT), butylated hydroxyanisole (BHA), tert-butylhydroquinone (TBHQ), lycopene, plant extracts, among others.

Cosmetic and Pharmaceutical Compositions

The cosmetic and pharmaceutical compositions comprising the antioxidant complex of the present invention may also comprise some components already known in the art.

The cosmetic and pharmaceutical compositions comprise from 0.003% to 3.000% by weight of the antioxidant complex of the present invention, based on the total weight of said compositions, and a carrier.

In preferred embodiments, the cosmetic and pharmaceutical compositions comprise an antioxidant complex composed of:
a) from 10 μg/ml to 200 μg/ml of Vitamin E;
b) from 10 μg/ml to 100 μg/ml of green tea extract;
c) from 10 μg/ml to 100 μg/ml of cacao extract,
wherein all amounts refer to the total weight of the composition and
a cosmetically and pharmaceutically acceptable carrier.

Emollient

Emollients perform different functions in cosmetic compositions, amongst which: adding or replacing lipids and natural oils to the skin, solubilizing sunscreens, imparting improved spreadability for applying the product, modifying the sensory map, etc.

Conventional lipids, such as oils, waxes, lipids and other waterinsoluble components and polar lipids, which are the lipids modified so as to increase water solubility by esterification of a lipid to a hydrophilic unit, such as, for example, hydroxy groups, carbonyl groups, among others, may be used as emollients to be added to the composition of the present invention. Some compounds which may be used as emollients are natural oils and plant derivatives, esters, silicone oils, polyunsaturated fatty acids, lanoline and derivatives thereof. Some natural oils which may be used are derived from apricot seed, sesame, soybean, peanut, coconut, olive, cocoa butter, almond, avocado, carnauba, cotton seed, rice bran, peach seed, mango seed, jojoba, *macadamia* nut, coffee, grape seed, pumpkin seed, among others, and mixtures thereof.

Some ethers and esters may also be used as emollients, such as, for example, $C_8$-$C_{30}$ alkyl esters of $C_8$-$C_{30}$ carboxylic acids, $C_1$-$C_6$ diol monoesters, and $C_8$-$C_{30}$ carboxylic acid diesters, $C_{10}$-$C_{20}$ alcohol sucrose monoesters, and combinations thereof. Examples of these compounds are dicaprylic acid, cetyl lactate, isopropyl palmitate, dicaprylyl carbonate, $C_{12-15}$ alkyl benzoate, isopropyl myristate, isopropyl isononate, sucrose palmitate, sucrose oleate, isostearyl lactate, glyceryl behenate, triglycerol-4 isostearate, pyrrolidone lauryl carboxylic acid, panthenyl triacetate, and combinations thereof. Silicones also act as emollients in the cosmetic and pharmaceutical compositions of the present invention. Some examples of silicone which may be added to said compositions are: volatile and non-volatile silicone oils, such as, for example, cyclomethicone, alkyldimethicones, dimethicone copolyols, dimethiconols, phenyl trimethicones, caprylyl trimethicones, aminofunctional silicones, phenyl-modified silicones, phenyl trimethicones, alkylmodified silicones; dimethyl and diethyl polysiloxane, mixed $C_1$-$C_{30}$ alkyl polysiloxane, dimethyl siloxanes, polymethylsiloxane, α-methyl-ω-methoxypolymethylsiloxane, polyoxydimethylsilylene, polydimethyl silicone oil, and combinations thereof or silicone elastomers, such as cyclomethicone crosspolymer and dimethicone, dimethicone vinyl crosspolymer and dimethicone, dimethicone crosspolymer and dimethicone, and cyclopentasiloxane crosspolymer and dimethicone.

Other fatty alcohols, mono-, di- or triglycerides having a lipophilic nature, such as dicaprylic acid, may also be used, in addition to synthetic and natural hydrocarbons, organic carbonates such as dicaprylic carbonate, some types of silicones such as cyclomethicone, and mixtures thereof.

Additionally, various natural compounds may be used as emollients, such as microcrystalline wax, carnauba wax, shea butter, bee wax, ozokerite wax, among others.

Sunscreens

In order to filter ultraviolet radiation, water-soluble or liposoluble sun protection agents may be added.

Some examples of sunscreens which absorb ultraviolet rays and which are suitable for addition to the cosmetic composition of the present application are the following: benzylidene camphor and derivatives thereof, isophthalylidene camphor and terephtalylidene camphor and derivatives thereof, cinnamic acid and esters thereof, salicylic acid and esters thereof, benzoic acid and esters thereof, p-aminobenzoic acid and derivatives thereof such as esters thereof, substituted hydroxybenzophenones, substituted dibenzoylmethane, benzotriazole and some derivatives such as 2-arylbenzotriazole, 2-arylbenzimidazole, 2-arylbenzofuranes, 2-arylbenzoxazole, 2-arylindol, mono-phenylcyanoacrylates, diphenylcyanoacrylates, among other ultraviolet ray filters known in the art.

Some examples of sunscreens that are suitable for the present invention are organic compounds, often having low water solubility, such as triazine derivatives (for example, hydroxyphenyltriane compounds or benzotriazole derivatives), some amides, such as the ones containing a vinyl group, cinnamic acid derivatives, sulfonated benzimidazoles, diphenylmalonitriles, oxalylamides, camphor derivatives, salicylic acid derivatives, such as 2-ethylhexyl salicylates, homosalates and isopropyl salicylates, diphenylacrylates, benzophenone derivatives, such as benzophenone-2, benzophenone-3, and benzophenone-4, PABA such as 2-ethylhexyl 4-dimethylaminobenzoate, and other sunscreens commonly added to sun protection product compositions.

In addition to the examples provided above, there are other preferred components to perform this function, such as: N,N,N-trimethyl-4-(2-oxoborn-3-ylidenemethyl) anilinium methyl sulfate; 3,3'-(1,4-phenylenedimethylene)bis(7,7-dimethyl-2-oxo-bicyclo-(2.2.1) 1-heptylmethanesulfonic acid and derivatives thereof; 1-(4 tert-butylphenyl)-3-(4-methoxyphenyl) propane-1,3-dione; α-(2-oxoborn-3-ylidene) toluene-4-sulfonic acid and potassium, sodium and triethanolamine salts thereof; 2-ethylhexyl 2-cyano-3-,3'-diphenylacrylate; 2-ethoxyethyl 4-methoxycinnamate; 2,2'-dihydroxy-4-methoxybenzophenone; methyl anthranilate; triethanolamine salicylate; 2,2',4,4' tetrahydroxybenzophenone; 2-phenylbenzimidazole-5-sulfonic acid and potassium, sodium and triethanolamine salts thereof; 2-ethylhexyl 4-methoxycinnamate; 2-hydroxy-4-methoxybenzophenone (oxybenzone); 2-hydroxy-4-methoxybenzophenone 5-sulfonic acid and its sodium salt (sulisobenzone and sodium sulisobenzone); 4-aminobenzoic acid (PABA); homomethyl salicylate; N-{(2 and 4) [(2 oxoborn-3-ylidene)methyl]benzyl}acrylamide polymer; titanium dioxide (with or without lipophilic coating); ethyl N-ethoxy-4-aminobenzoate; 2-ethylhexyl 4-dimethylaminobenzoate; 2-ethylhexyl salicylate; isopentyl 4-methoxycinnamate; 3-(4'-methylbenzylidene)-d-1-camphor; 3-benzylidene camphor: 2,4,6-trianilin-(p-carbo-2'-ethyl-hexyl-1'-oxy)-1,3,5-octyl triazine; zinc oxide (with or without lipophilic coating); 2-(2H-benzotriazol-2-yl)-4-methyl-6-{2-methyl-3-(1,3,3,3-tetramethyl-1-((trimethylsilyl)oxy)disiloxanyl) propyl}phenol; benzoic acid; 4,4'-[[6-[[4-[[(1,1-dimethyl-ethyl)amino]carbonyl]phenyl]amino]-1,3,5-trazine-2,4-diyl]diimino]bis, bis(2 ethylhexyl); 2,2'-methylene-bis-6-(2H-benzotriazol-2-yl)-4-(tetramethyl butyl)-1,1,3,3-phenol; methylene bis-benzotriazolyl tetraethyl butyl phenol; 2,2'-bis-(1,4-phenylene)-IH-benzimidazol-4,6 disulfonic acid monosodium salt; (1,3,5)-triazine-2,4-bis {[4-(2-ethyl-hexyloxy)-2-hydroxy]-phenyl]-6-(4-methoxyphenyl); bisethylhexyloxyphenol methoxyphenyl triazine; methylene bis-benzotriazolyl tetramethylbutylphenol; butyl methoxydibenzoylmethane, 2-ethylhexyl pmethoxycinnamate, methylene bis-benzotriazolyl tetramethylbutylphenol, 4-butyl-4-methoxydibenzoylmethane, benzophenone 3, bisethylhexyloxyphenol methoxyphenyl triazine, octyl triazone, titanium dioxide, cinnamidopropyltrimonium chloride, dimethylpabamidopropyl laurdimonium tosylate.

There are still other sunscreens that can also be used to protect the skin, such as iron oxide, titanium dioxide combined with simethicone, zinc oxide, mono- or polycarbonyl compounds such as isatine, alloxan, ninhydrin, glyceraldehyde, mesotartaric aldehyde, glutaraldehyde, pyrazolin-4,5-dione or 4,4-dihydroxypyrazolin-5-one derivatives, methylglyoxal, 2,3-dihydroxysuccinic dialdehyde, 2-amino-3-hydroxysuccinic dialdehyde and 2-benzylamino-3-hydroxysuccinic dialdehyde.

Carrier

Water is the basis of various possible cosmetic compositions prepared with the antioxidant complex already described, acting as a carrier for the other components. The compositions of the present invention comprise water, preferably demineralized or distilled, at the percentage required (q.s.p.) to reach 100% of the formula based on the total weight of the present composition. Naturally, other cosmetically acceptable carriers may be used in the present invention. In the examples of compositions which will be described below, 96° GL ethyl alcohol, oily carriers (oils in general, waxes and butters), silicone carriers, among others, are also used as carriers.

Other Optional Components

In order to provide the cosmetic and pharmaceutical compositions of the present invention with a desirable characteristic not obtained with the components already mentioned, optional components that are compatible with the properties of said compositions may be further added. Some of the compounds which may be added to said compositions are as follows:

- Active ingredients (whether encapsulated or not): these may be lipophilic or hydrophilic, such as seaweed extracts, plant extracts, a combination of palmitoyl hydroxypropyltrimonium aminopectin, glycerin crosspolymer, lecithin and grape seed extract, alpha bisabolol (anti-inflammatory active ingredient), D-panthenol (conditioning active ingredient), biosaccharide gum 2 and biosaccharide gum 3, and other active ingredients commonly added to topical compositions;
- Bacteriostats, bactericides or antimicrobials;
- An emulsifier such as potassium cetyl phosphate, among others;
- Stabilizers, such as sodium chloride, among others;
- A sequestering agent, such as ethylenediaminetetraacetic (EDTA) and salts thereof, among others;
- A pH adjusting agent such as triethanolamine, sodium hydroxide, among others;
- A preservative, such as phenoxyethanol, PEG-5 cocoate and PEG-8 dicocoate, iodopropynyl butylcarbamate and PEG-4, among others;
- Natural or synthetic dyes;
- Thickening agents such as xanthan gum and carbomer, among others;
- Plant extracts: chamomile, rosemary, thyme, *calendula*, carrot extract, juniper extract, gentian extract, cucumber extract, among others;
- Skin conditioning agents; and
- Other cosmetically acceptable components that are compatible with the antioxidant complex of the present invention.

EXAMPLES OF COMPOSITION

The examples below are preferred embodiments of compositions comprising the antioxidant complex of the present invention and should not be interpreted as limitations thereof. In this sense, it is to be understood that the scope of the present invention encompasses other possible embodiments and is limited only by the content of the appended claims, including therein the possible equivalents.

Example 1

Emulsion without Sunscreens

| Component | Function | Amount by weight (%) |
|---|---|---|
| Water | Carrier | Qsp 100 |
| C12-15 alkyl benzoate | Emollient | 5.00 |
| Glycerin | Humectant | 5.00 |
| Dicaprylyl carbonate | Emollient | 2.00 |
| Potassium cetyl phosphate | Emulsifier | 2.00 |
| Cyclomethicone | Emollient | 2.00 |
| Phenoxyethanol | Preservative | 1.00 |
| Dimethicone copolyol methyl ether | Emollient | 0.50 |
| Vitamin E acetate | Antioxidant | 2 |
| PEG-5 cocoate and PEG-8 dicocoate and iodopropynyl butylcarbamate and PEG-4 | Preservative | 0.20 |
| disodium EDTA | Sequestering agent | 0.10 |
| BHT | Antioxidant | 0.05 |
| *Cacao* extract | Antioxidant | 0.1 |
| Green tea extract | Antioxidant | 0.1 |

-continued

| Component | Function | Amount by weight (%) |
|---|---|---|
| Xanthan gum | Thickening agent | 0.20 |
| Carbomer | Thickening agent | 0.35 |
| Triethanolamine | pH adjuster | 0.50 |

Example 2

Emulsion with Sunscreens

| Component | Function | Amount by weight (%) |
|---|---|---|
| Water | Carrier | Qsp 100 |
| 2-ethylhexyl p-methoxycinnamate | Sunscreen | 7.50 |
| C12-15 alkyl benzoate | Emollient | 6.00 |
| Glycerin | Humectant | 5.00 |
| Benzophenone 3 | Sunscreen | 5.00 |
| Dicaprylyl carbonate | Emollient | 4.00 |
| Cyclomethicone | Emollient | 3.00 |
| Titanium dioxide and simethicone | Sunscreen | 3.00 |
| Bis-ethylhexyloxyphenol methoxyphenyl triazine | Sunscreen | 2.00 |
| Aluminum starch octenylsuccinate | | 1.50 |
| Potassium cetyl phosphate | Emulsifier | 2.00 |
| Cyclomethicone and dimethicone copolyol | Emollient | 1.00 |
| Phenoxyethanol | Preservative | 1.00 |
| Vitamin E acetate | Antioxidant | 2 |
| PEG-5 cocoate and PEG-8 dicocoate and iodopropynyl butylcarbamate and PEG-4 | Preservative | 0.20 |
| disodium EDTA | Sequestering agent | 0.10 |
| BHT | Antioxidant | 0.05 |
| *Cacao* extract | Antioxidant | 0.1 |
| Green tea extract | Antioxidant | 0.1 |
| Xanthan gum | Thickening agent | 0.20 |
| Carbomer | Thickening agent | 0.40 |
| Triethanolamine | pH adjuster | 0.50 |

Test Examples

Description of the Methodologies

The methodologies selected for planning and carrying out the tests for the antioxidant efficacy of the complex of the present invention aimed at reproducing the protective effect of membranes (lipids), DNA and proteins, and were fast screening methodologies, such as:

DPPH: the test is based on the reduction reaction of the diphenyl picryl hydrazyl (DPPH) free radical in ethanolic medium, with the raw materials or substances to be analyzed, wherein the DPPH radical is reduced by said substances, altering the tone and enabling the antioxidant protection to be measured. This is a simple assay, commonly used for screening substances, since it measures one of the main mechanisms of antioxidant action—proton donation for stabilization of the DPPH radical.

Lipoperoxidation: in this test, phosphatidylcholine liposomes, which structure resembles the cell membrane since phosphatidylcholine is one of the lipid components of cell membranes, are incubated with the AAPH radical, which is capable of promoting the oxidation of these membranes, forming lipid hydroperoxides. These hydroperoxides promote the oxidation of $Fe^{2+}$ to $Fe^{3+}$, which reacts with xylenol orange, forming a yellowish compound. The active ingredients incubated with the liposomes decrease the membrane oxidation, consequently decreasing the reaction with xylenol orange and the formation of color. This test provides a result for the % protection against lipoperoxidation, and is closer to the physiological situation, since it mimics the attack to cell membranes.

Protein Oxidation: this experiment uses BSA (bovine serum albumine) as a substrate and a hydroxyl radical generating system (Fenton reaction: $H_2O_2$+ iron), which can generate hydroperoxides in the presence of the protein, due to the oxidation of the amino acid side chain. These hydroperoxides promote the oxidation of Fe2+ to Fe3+, which reacts with xylenol orange, forming a yellowish compound. The active ingredients are incubated with BSA and with the free radical generating system, which are expected to protect the protein from the oxidative attack of the hydroxyl radicals.

Plamid DNA Oxidation: in this test, the plasmid DNA from bacteria is exposed to UVA radiation in the presence of a photosensitizer—riboflavin. This reaction increases ROS formation and consequently results in the breakdown of the plasmid DNA. This breakdown is perceived in the agarose gel run, where only one band is observed for nonradiated samples, and more than one for radiated samples. Active ingredients which provide protection against oxidative breakdown of plasmid DNA should cause radiated DNA samples containing the active ingredient to maintain the same profile as the nonradiated samples.

Tests for Assessing the Individual Antioxidant Activity of the Active Ingredients Selected for the Mixture:

The individual assessment of each active ingredient was started. In this step, the lipoperoxidation methodology which mimics the oxidation of cell membranes was selected for the final decision regarding the active ingredients to be made. However, DPPH was also used, since it is a very useful screening methodology for comparing the potency of the active ingredients.

DPPH:

This methodology is used to assess the IC-50 value, i.e., the amount of active ingredient required to neutralize 50% of the radicals formed in the reaction medium. The lower the value, the more potent the active ingredient.

Table 1 below lists IC-50 values (%; mg/ml; µg/ml) for the selected active ingredients:

Table 1:

TABLE 1

| Active Ingredient | IC-50 (%) | IC-50 (mg/ml) | IC-50 (µg/ml) |
| --- | --- | --- | --- |
| Green tea extract 1* (Cognis) | 2.6E−04 | 0.0026 | 2.6 |
| Green tea extract Ayalla | 3.3E−04 | 0.0033 | 3.3 |
| *Cacao* extract | 7.0E−04 | 0.007 | 7 |
| Tocopherol | 1.9E−03 | 0.019 | 19 |
| Green tea extract CF | 7.1E−04 | 0.0071 | 7.1 |
| Açai Palm 30 | 9.0E−04 | 0.009 | 9 |
| Unichem Coffee | 1.1E−03 | 0.011 | 11 |
| Ayalla Rosemary | 1.3E−03 | 0.013 | 13 |
| Coffee CF | 2.3E−03 | 0.023 | 23 |
| Provital Rosemary | 5.2E−03 | 0.052 | 52 |
| Pariparoba Plant | 7.0E−03 | 0.07 | 70 |

TABLE 1-continued

| Active Ingredient | IC-50 (%) | IC-50 (mg/ml) | IC-50 (µg/ml) |
| --- | --- | --- | --- |
| Açai Palm | 1.0E−02 | 0.1 | 100 |
| Lycopene | 2.1E−02 | 0.208 | 208 |
| Line Açai Palm | 5.7E−02 | 0.574 | 574 |

The values obtained in the two previous tests had been compared and was verified that the active ingredients that provided greater protection for DPPH, not necessarily offered the best protection against the lipoperoxidation. This is mainly due to the different characteristic of the active ingredients and the assays. For this reason, some specific criteria were established for each methodology in order to determine which active ingredients would have to continue to be tested.

DPPH: considering the characteristics of the assay, some ranges had been established to classify the active ingredients in relation to the antioxidant potency:

HIGHEST antioxidant potency: substances that provide high protection in very low concentrations –IC-50 (%) in the magnificence of $10^{-4}$. Green Tea and Cacao are classified herein.

HIGH antioxidant potency: substances that provide high protection in low concentrations –IC-50 (%) in the magnificence of $10^{-3}$. Pariparoba, Rosemary, Tocopherol and Coffee are classified herein.

MEDIUM antioxidant potency: substances that have provide high protection in very low concentrations –IC-50 (%) in the magnificence of $10^{-2}$. Açai Palm and Lycopene are classified herein.

As the DPPH test evaluates a specific radical for a specific reduction mechanism, it is important that the active ingredient be capable to neutralize the radical in very low concentrations. Thus, it was established as criterion to continue working with the active ingredients that provide the HIGH or HIGHEST antioxidant protection.

Lipoperoxidation:

This methodology is used to assess the percentage protection of the active ingredients against lipoperoxidation in 3 hours of reaction. The concentration of the active ingredients was set at 100 µg/ml (0.01%) for the purpose of comparing the protective potency of each of them.

A list of the results obtained in the lipoperoxidation assessment is provided below:

Lycopene: 25.30%
Cacao Extract (*Theobroma cacao*): 51.60%
Rosemary (Provital): 52.09%
Green Tea Extract (*Camellia sinensis*): 64.89%
Coffee (Unichen): 72.49%
Tocopherol: 95.53%

As all the active ingredients were tested in low a concentration (0.01%), it was determined that the active ingredients that were capable of providing protection of at least 50% against the lipoperoxidation even in low concentrations, would be active with high potency and, therefore, they would continue to be tested, namely: Cacao, Rosemary, Green Tea, Coffee and Tocopherol. Rosemary, however, was not further tested due to its possible abortive effect. Therefore, additional studies were carried out for Cacao, Green Tea, Coffee and Tocopherol.

Selection of the Complex:

The four components were assessed as follows:

Active ingredients 2×2: Cacao+Green tea; Cacao+Coffee; Coffee+Green tea;

Active ingredients+TOCOPHEROL: (3) Cacao+tocopherol; (2) Green tea+tocopherol; Coffee+tocopherol Active ingredients+TOCOPHEROL: (4) Cacao+Green tea+Tocopherol; Cacao+Coffee+tocopherol; Green tea+Coffee+tocopherol.

The μg/ml concentrations of the mixtures tested and the percentage results for protection against lipoperoxidation (3h) are summarized below in table 2 of this report.

TABLE 2

|  | Cacao | Coffee | Green tea | Tocopherol | Total active ingredients | Protection %: |
|---|---|---|---|---|---|---|
| Mixture 1 | 100 | 10 | — | — | 110 | 47.3 |
|  | 50 | 5 | — | — | 55 | 46.7 |
|  | 10 | 25 | — | — | 35 | 37.2 |
| Mixture 2 | — | 10 | 10 | — | 20 | 52.7 |
|  | — | 5 | 5 | — | 10 | 20.0 |
| Mixture 3: | 10 | — | 10 | — | 20 | 35.3 |
|  | 10 | — | 25 | — | 35 | 35.3 |
|  | 10 | — | 5 | — | 15 | 26.4 |
| Mixture 4 | — | 10 | — | 10 | 20 | 5.2 |
| Mixture 5: | — | — | 7 | 10 | 17 | 32.6 |
| Mixture 6: | 25 | — | — | 10 | 35 | 38.1 |
| Mixture 7 | — | 10 | 10 | 200 | 220 | 53.1 |
|  | — | 10 | 10 | 100 | 120 | 60.3 |
|  | — | 10 | 10 | 25 | 45 | 58.9 |
|  | — | 3 | 3 | 33 | 39 | 66.3 |
| Mixture 8 | 100 | 10 | — | 200 | 310 | 57.7 |
|  | 100 | 10 | — | 50 | 160 | 55.1 |
|  | 100 | 10 | — | 25 | 135 | 54.3 |
|  | 30 | 3 | — | 30 | 63 | 65.2 |
| Mixture 9: | 10 | — | 10 | 10 | 30 | 69.4 |
|  | 10 | — | 10 | 25 | 45 | 68.4 |

The highest protection value by mixture (reached with mixture 9) is shown in the graph illustrated in FIG. 1 of the present specification.

The assessment of the amount of active ingredients required to reach the highest protection percentage, based on the mixture which provided maximum protection at the smallest dosage, showed that the mixture of cacao extract+green tea extract+tocopherol is the most effective one. Thus, an effective antioxidant complex having a low concentration of active ingredients, a high degree of "vegetalization" (use of renewable material of plant origin) and results above expectations was obtained.

Figure 2:
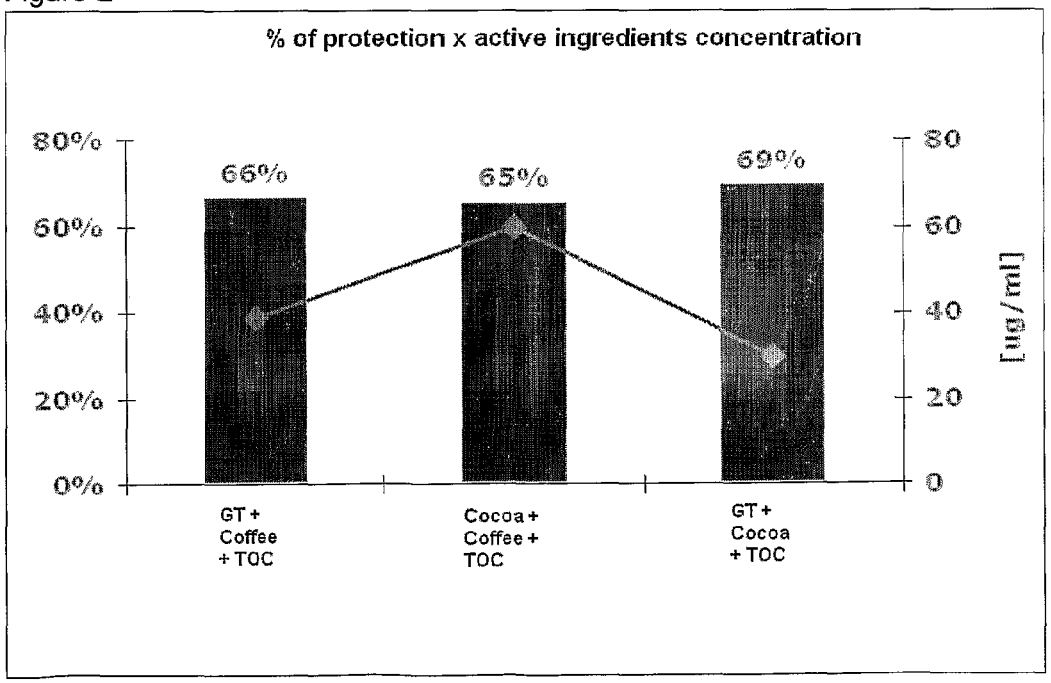
FIG. 2 illustrates a graph showing the percentage of protection against lipoperoxidation vs total concentration of active ingredients of the most effective mixtures.

The most effective mixtures are shown in FIG. 2 wherein the percentage of protection against lipoperoxidation versus total concentration of active ingredients are demonstrated.

As can be concluded from the table above, the mixture of 10 μg/ml of green tea, 10 μg/ml of cacao, and 10 μg/ml of tocopherol, totalizing 30 μg/ml of active ingredients, provides a high percentage of protection against lipoperoxidation in 3 hours, 69.44%.

The amount of each active ingredient required to provide a degree of protection similar to the one obtained with the mixture (between 60 and 70% protection) was assessed. The data used for the purposes of this analysis were those of the tested concentration which provided the protection result closest to 69.44%. However, as can be seen from the table above, other combined concentrations also provide the optimized and positive effect of protection against oxidation.

Figure 3:
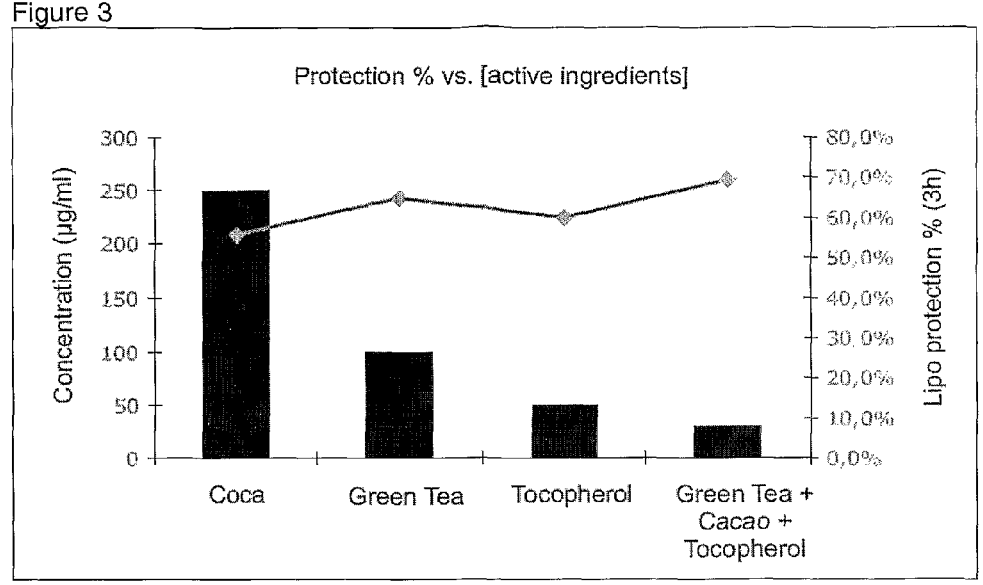
FIG. 3 illustrates a graph showing the percentage of protection against lipoperoxidation obtained with the concentration of active ingredients in isolation vs. the one obtained with the concentration of active ingredients in the mixture.

The graph relating to the concentration of active ingredients in isolation vs. concentration of active ingredients in the mixture is illustrated in FIG. 3 of this specification. The line represents the percentage of protection against lipoperoxidation of each mixture and/or active ingredient, and the columns represent the concentration of active ingredients for each sample assessed.

It should be noted that a tocopherol concentration at least 5 times higher, a green tea extract concentration at least 10 times higher, and a cacao extract concentration at least 25 times higher than the concentrations used in the mixture would be required to reach a degree of protection similar to the one provided by the mixture of antioxidants. Thus, it is concluded that the interaction of these active ingredients is positive for the antioxidant activity. These data clearly show that the said result could not be expected. The final result reached exceeds the one which would have been obtained based on the analysis of the active ingredients in isolation.

Evaluation of the Effectiveness of New Antioxidant Complex x CurRent Antioxidant Complex After defining which was the more effective antioxidant mixture according the present invention ("new" antioxidant complex), other antioxidant effectiveness tests were been carried out for activity comparison between the mixture of the present invention and a conventional antioxidant complex, as follows:

Lipoperoxidation:

An antioxidant complex comprising lycopene (20 ug/ml), coffee extract (20 ug/ml) and tocopherol acetate (equivalent to 100 ug/ml), totalizing 140 ug/ml provides a protection of 70.41% against the lipoperoxidation (3h) which is a result that can be considered equal to the result for the new mixture (69.44%).

However, in the new proposed mixture, a concentration of total active ingredients of 30 ug/ml is used, that is, 4, 7 times less than the concentration used in the mixture of the known antioxidant complex. Thus, it can be concluded by this test, that the new proposed mixture has potency 4, 7 times higher than the mixture currently used.

DPPH:

In the DPPH test the mixture of the present invention provided 96% of protection. Upon comparing the amount of active ingredients necessary to neutralize 50% of the radicals (IC-50) in the new mixture to the one of the known antioxidant complex, it is observed that the first one has greater activity potency (lower value of IC-50), as already had been observed through the lipoperoxidation protocol:

Test for Assessing Protection Against Plasmid DNA Oxidation:

This test was carried out with the samples detailed in table 3 below:

TABLE 3

| Sample | Treatment |
|---|---|
| 1 Control without riboflavin | Radiated |
| 2 Control without riboflavin | Nonradiated |
| 3 Green tea + *Cacao* + TOC (antioxidant complex (730A)) | Radiated |
| 4 Green tea + *Cacao* + TOC (antioxidant complex (730A)) | Nonradiated |
| 5 Green tea + *Cacao* + TOC (10x) (New antioxidant complex + 10) | Radiated |
| 6 Green tea + *Cacao* + TOC (10x) (New antioxidant complex + 10) | Nonradiated |
| 7 Green tea + *Cacao* + TOC (1/10) (New antioxidant complex − 10) | Radiated |
| 8 −Green tea + *Cacao* + TOC (1/10) (New antioxidant complex − 10) | Nonradiated |
| 9 Line antioxidant complex (729A) | Radiated |
| 10 New antioxidant complex (729A) | Nonradiated |

Figure 4:
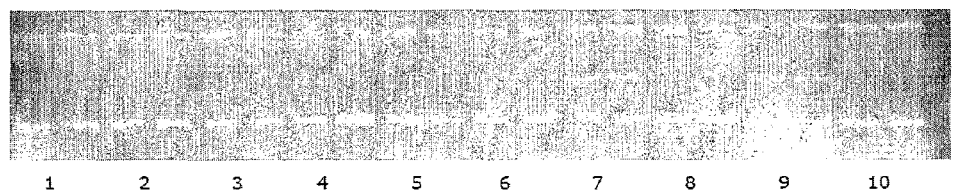
FIG. 4 illustrates a graph showing the result of the plasmid DNA oxidative breakdown assessment.

FIG. 4 illustrates the result of the assessment of plasmid DNA breakdown.

New antioxidant complex +10 means that a concentration of anti-oxidant complex 10× superior to that initially proposed was used and the new antioxidant complex –10, 10× inferior to the indicated concentration. Nonradiated controls were carried out for each sample and a control without riboflavin was also tested (the reaction does not occur). The results can be seen in FIG. 4.

Based on this graph, it can be concluded that the nonradiated sample of the mixture (4) has the same profile as the radiated sample (3), which means that this mixture protects the DNA against the oxidative attack. The same result was obtained with the 10× concentrated mixture. It can be concluded that in the 10× diluted sample the DNA is not protected (in sample 7, which has been radiated, DNA breakdown representative bands are observed, unlike in the nonradiated control, sample 8). Finally, it is also possible to conclude that the known antioxidant complex is not capable to protect the oxidative DNA breakdown (sample 9—radiated—presents representative bands of DNA breakdown, different to the nonradiated control, sample 10).

Figure 5:
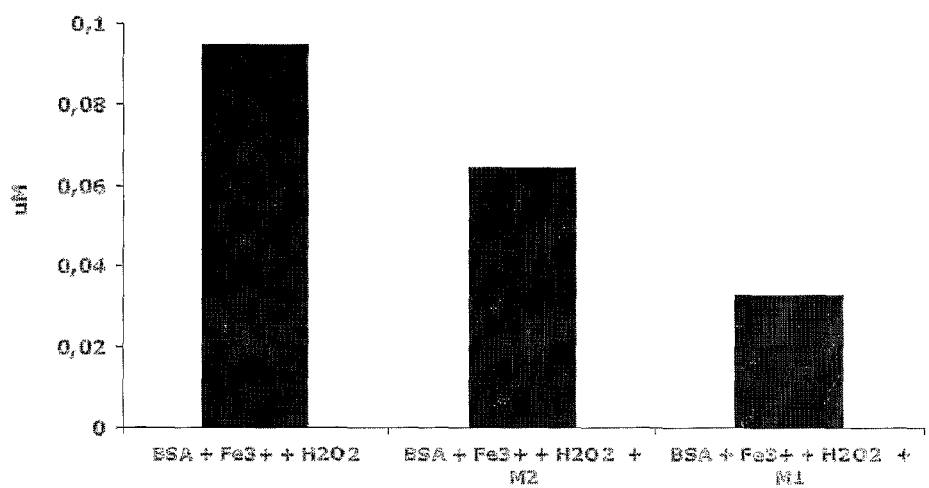
FIG. 5 illustrates a graph showing hydroperoxide formation: control and sample reactions.
Figure 5A:
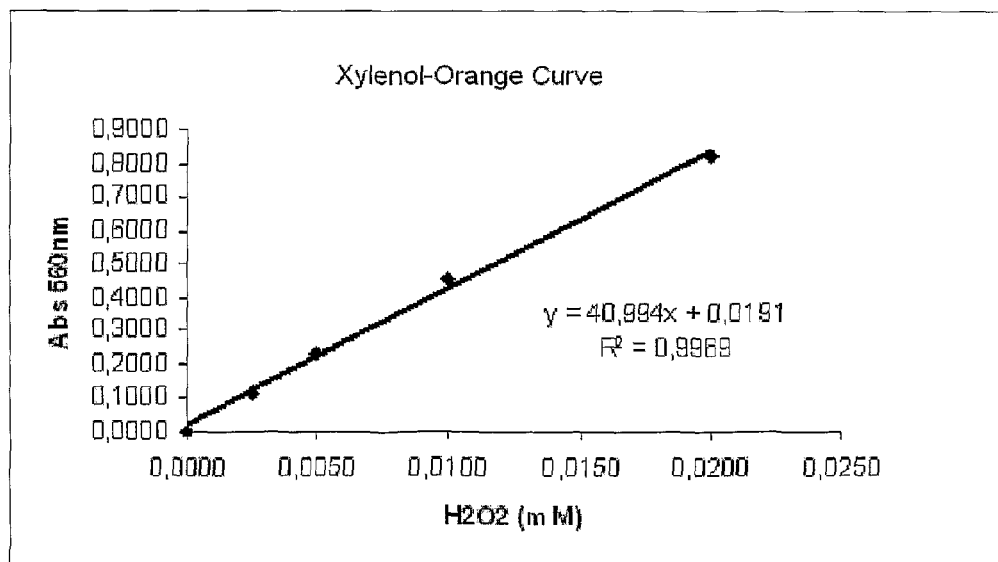
FIG. 5A illustrates a graph showing xylenol-orange curve with $H_2O_2$.
Figure 5B:
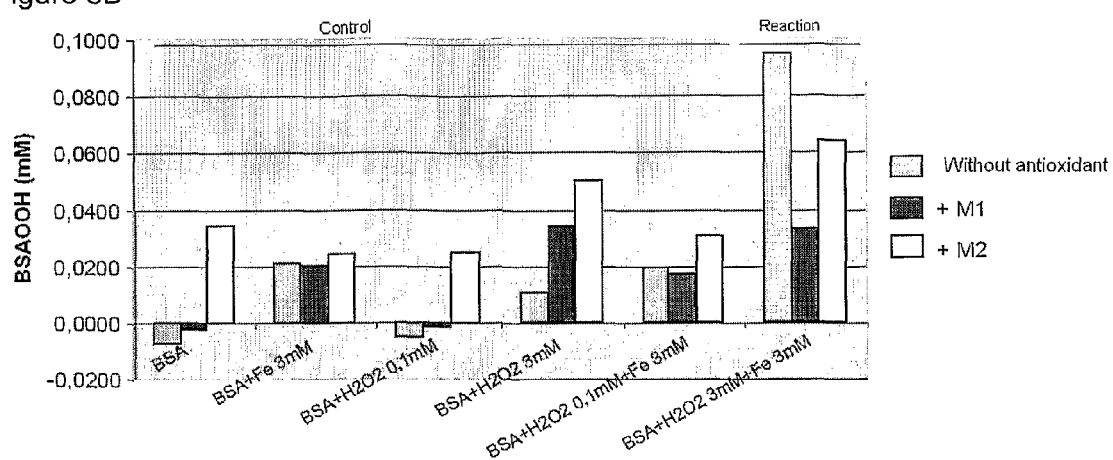
FIG. 5B illustrates a graph the hydroperoxide formation; controts and samples (reaction)

Test for Assessing Protection Against Protein Oxidation:

This test was used to assess the ability of the mixture in question (M1: green tea+cacao+tocopherol) and of the known antioxidant complex (M2: lycopene+coffee+tocopherol) to protect against protein oxidation (in this case, BSA). The results obtained are shown in FIGS. 5, 5A and 5B.

This assay assesses the formation of protein hydroperoxides by xylenol orange, and therefore the construction of a curve of xylenol with hydrogen peroxide is required.

One notices that in the controls M2 (known antioxidant complex) presented an oxidation level superior to the one observed in the control without active ingredients or in the control with M2. This possibly happened, due to the presence of metals weighed in the component extracts of the mixture that could, to speed up the oxidation of the BSA.

The assessment of the result obtained for the best oxidation condition established (reaction) shows that the two mixtures is are able to protect BSA against oxidation generated by hydroxyl radicals, however, M1 (new antioxidant complex) provides 65% of protection, while mixture 2 provides 32% of protection. This assay has also proved that the mixture in question is more potent than the mixture of reference.

Test for Assessing the Ability to Neutralize Free Radicals:

This assay is used to assess the active ingredient's ability to decrease the formation of free radicals. A specific radical (DPPH) produces a purple coloring in ethanolic solution. Antioxidant active ingredients capable of donating protons ($H^+$) decrease the formation of radicals, consequently decreasing the purple coloring.

The mixture in question (Green tea+Cacao+Tocopherol) was assessed at different concentrations (from 0.3 µg/ml to 300 µg/ml) and the results indicate that at a concentration of 15 µg/ml of the mixture a protection above 90% is already obtained.

Figure 6:
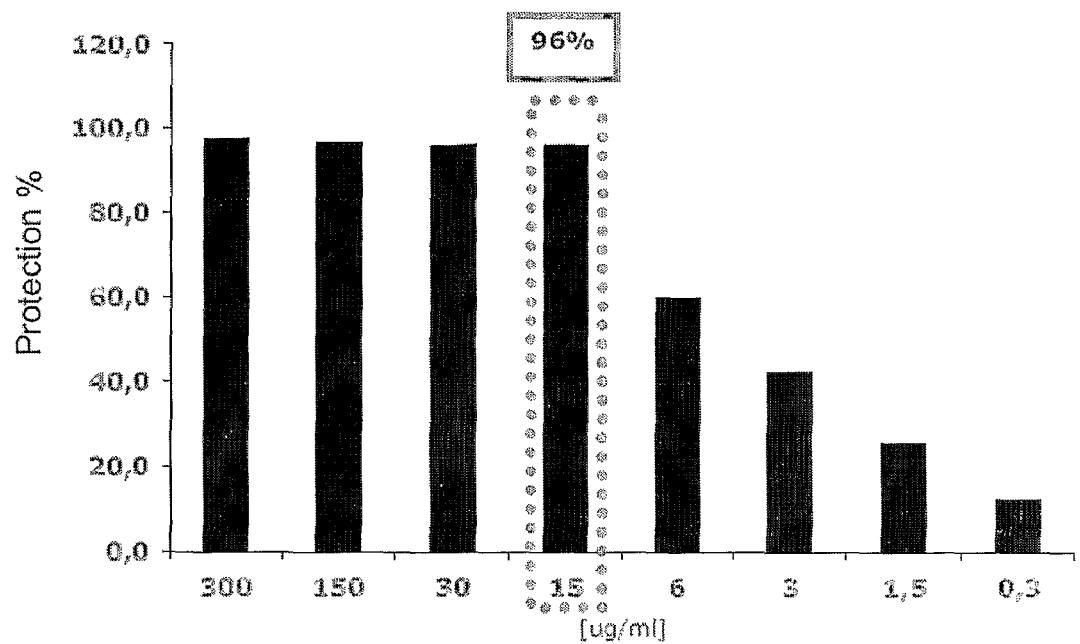
FIG. 6 illustrates a graph showing the DPPH (free radical neutralization) achieved with the present invention.

The results of this test are shown in the graph of FIG. 6. Thus, it has been concluded that a high degree of protection against the action of free radicals is obtained using small amounts of the antioxidants of the composition of the present invention.

Formation of CPD's (Pirimidine Dimers)

Figure 7:
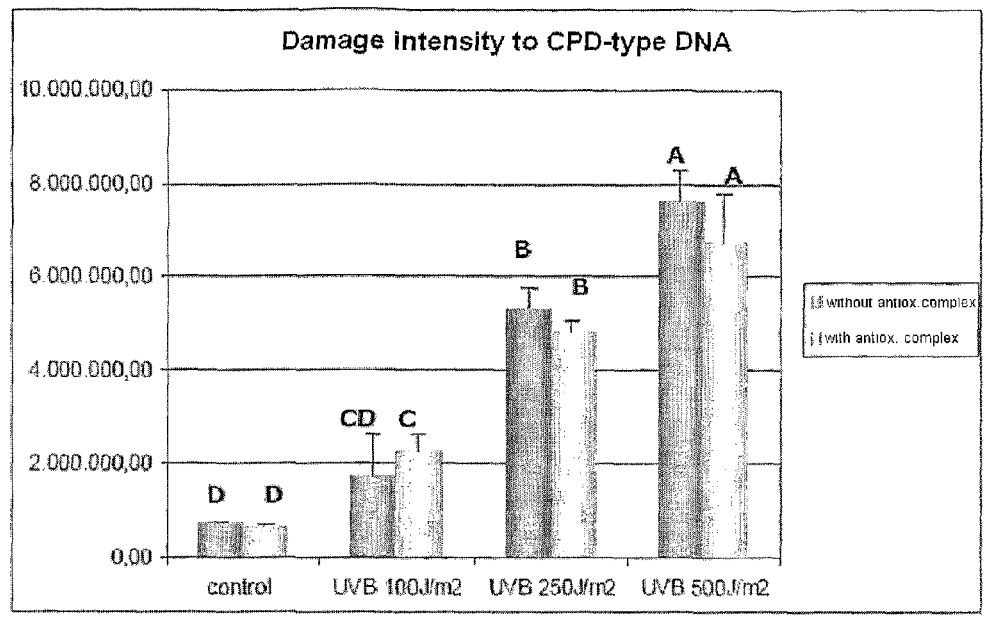
FIG. 7 illustrates a graph showing the damage intensity to CPD-type DNA with or without antioxidant complex.

In this assay it was evaluated whether the mixture according to the present invention would be capable to protect the DNA of the direct damages of UVB radiation, measured through the quantification of CPD's (pirimidine dimers—mutation commonly formed when the cells are exposed to UVB). As evaluated substances are antioxidants, one expects that they act protecting the DNA in an indirect form, that is, through the neutralization of free radicals that would attack the DNA bases (as it was demonstrated with the plasmidial DNA protocol). This test was carried out to investigate if the same active ingredients could have some protection activity and/or repair of the DNA against the direct damages (mutations) caused by UVB radiation. The results obtained are shown in FIG. 7.

It can be concluded from the results that the proposed mixture is not capable to protect the DNA from the direct damages caused by UVB radiation. It can be said, however, by the result of the plasmidial DNA test that it protects the DNA from the indirect damages of the radiation (in this in case, oxidative attack).

Antioxidant Activity in Fibroblasts

In this test it was evaluated antioxidant activity of the active ingredients mixtures (new and known antioxidant complex). In the assay, human fibroblasts are exposed to LPS so as to lead to the generation of reactive species of oxygen, mainly hydrogen peroxide. The peroxide thus formed oxidizes dichlorofluorescein (DCFH-DA) which becomes fluorescent. The measure of fluorescence is carried out through one flow cytometer and the result is the comparison of the control cells with the cells treated with the mixtures of active ingredients.

Figure 8:
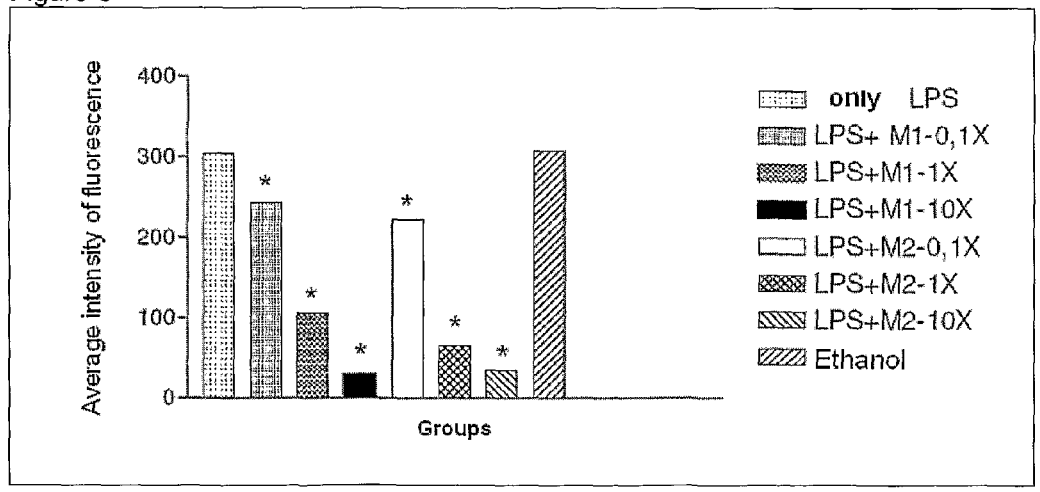
FIG. 8 illustrates a graph showing the damage intensity to CPD-type DNA with or without antioxidant complex.
Figure 9:
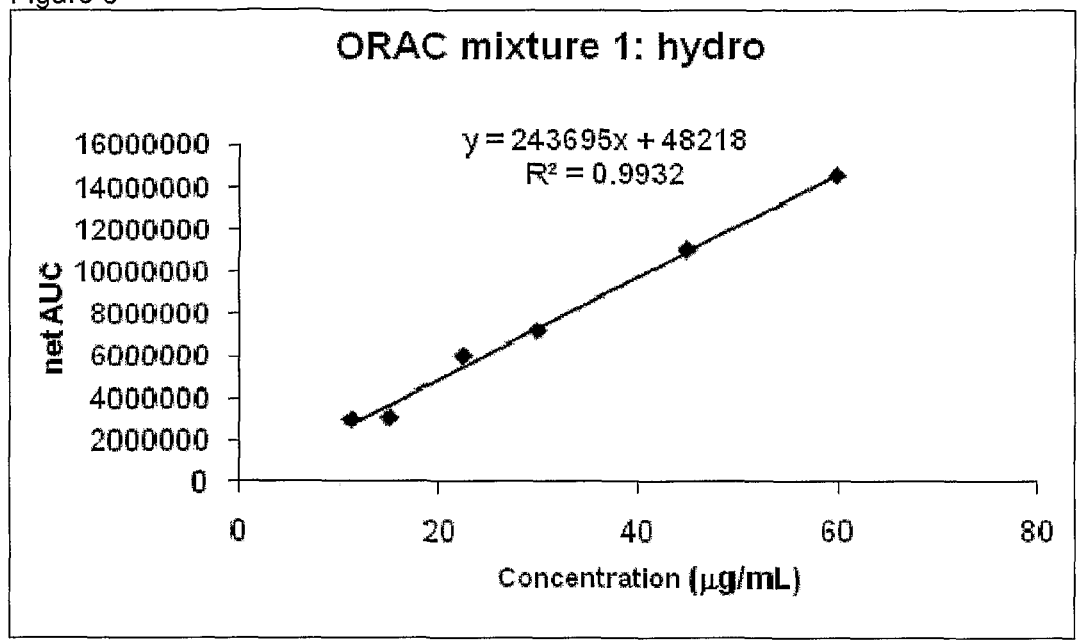
FIG. 9 illustrates a graph showing the fluorescence intensity for the measure of antioxidant activity, wherein M1 represents the mixture of the new antioxidant complex and M2 from the known antioxidant complex.
Figure 10:
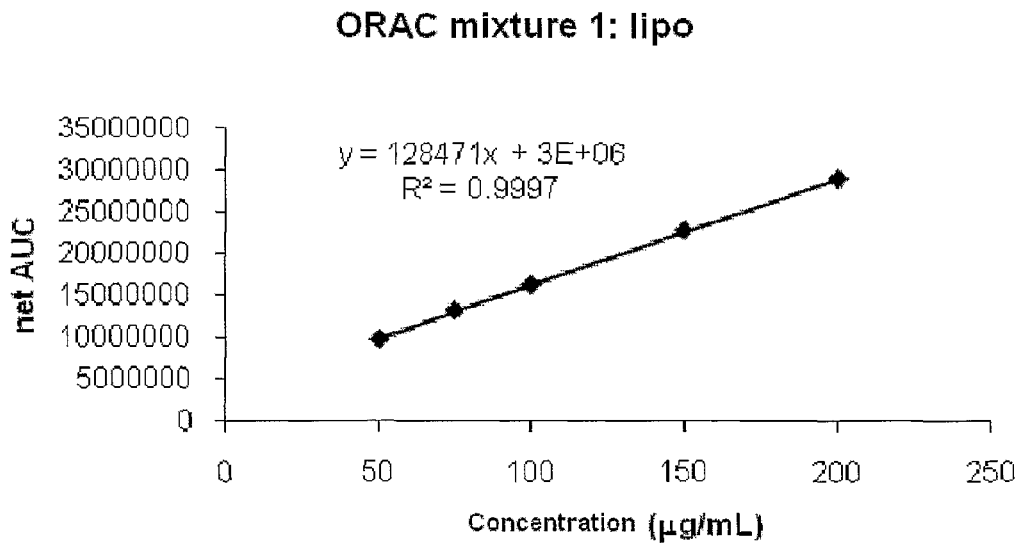
FIG. 10 illustrates a graph showing the relationship between the concentration and the inhibition of the decline of fluorescence to the sample mixture 1 by lipophilic method.
Figure 11:
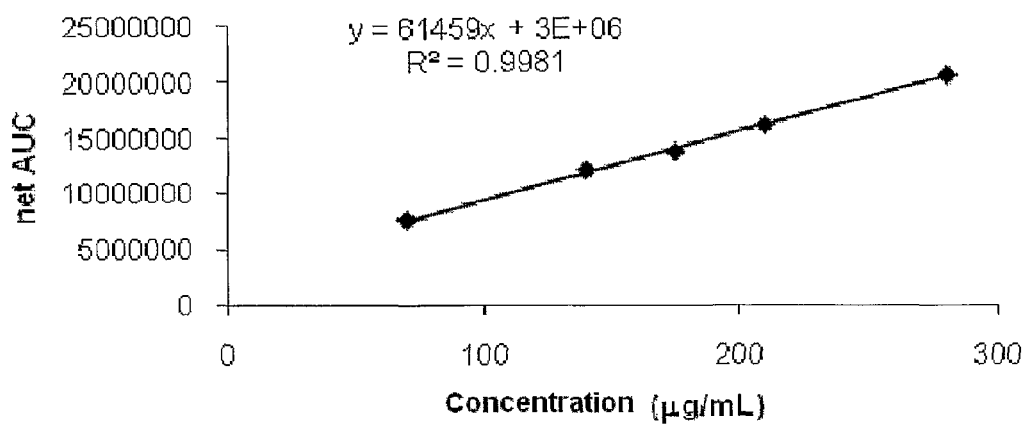
FIG. 11 illustrates a graph showing the relationship between the concentration and the inhibition of the decline of fluorescence to the sample mixture 2 by hydrophilic method.
Figure 12:
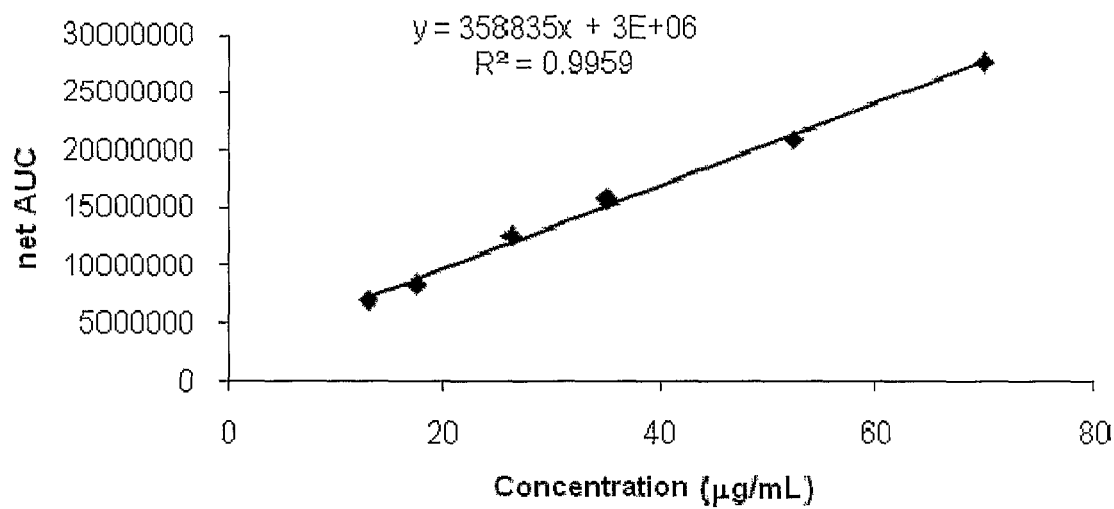
FIG. 12 illustrates a graph showing the relationship between the concentration and the inhibition of the decline of fluorescence to the sample mixture 2 by lipophilic method.

The results obtained demonstrate that both new and known anti-oxidant complexes are capable to significantly reduce the oxidative stress formed in a cell culture exposed to the LPS as shown in FIG. 8, wherein the two mixtures were assessed in their original concentrations, diluted 10 folds (0.1×) and 10 fold concentrated (10×).

Cellular Senescence (New Antioxidant Complex)

The cellular senescence is a multi-factorial process and the oxidative stress is one of the responsible ways for the beginning of this process. For this reason, it was investigated the activity of the antioxidant complex according to the present invention in reducing the state of cellular senescence. In this assay, the cells are exposed to UV radiation for 04 days and after this period one of the senescence markers—beta-galoctosidase enzyme—is measured to evaluate the state of the cells. The group treated with the new antioxidant complex presented less senescent cells in comparison with the standard. This result is represented by the less amount of marked cells with the beta-gal, as shown below on table 5:

TABLE 5

| SAMPLE | UVB – (% positive cells) | UVB + (% positive cells) |
| --- | --- | --- |
| Control | 11.67 ± 0.60 | 51.67 ± 1.36 |
| New antioxidant complex | 14.58 ± 0.92 | 38.81 ± 0.91 |

The results demonstrate that radiation UV (UVB-) non-exposed cells do not keep a senescence basal level. When exposed to radiation UV (UVB+), the number of marked cells for senescence increases, however, comparing the control with the group treated with the new antioxidant complex, it notices that the last one is capable to significantly reduce the number of positive beta-gal cells and, therefore, the state of cellular senescence.

Evaluation of the In Vitro Antioxidant Potential by ORAC Hydrophilic and Lipophylic Method ORAC Method provides a controlled source of peroxyl radicals that simulates the oxidative reactions with lipids in foods, cosmetics and physiological systems.

The system comprises a generating substance of free radical, the AAPH (2,2'-azobis (2-amidinopropane)dihydrochloride) and a fluorescent marker, fluorescein. The antioxidant substance presence in the reaction medium inhibits the decline of the induced fluorescence by the free radical.

The final value is calculated by the regression equation between the sample concentration and the area under the decline curve of fluorescence (AUC). Being expressed the result in micromoles equivalent of Trolox®/g of the sample.

$$AUC = 1 + f_1/f_0 + f_2/f_0 + f_3/f_0 + \ldots + f_n/f_0$$

$f_0$: initial fluorescence t=0 minutes $f_n$: fluorescence in each sample in t=n minutes $$\frac{(AUX_{sample} - AUC_{control})}{(AUC^{®}_{trolox} - AUC_{control})} \times \frac{\text{molarity } Trolox^{®}}{\text{concentration sample}}$$

Considering net $AUC = AUC_{sample\ or\ Trolox} - AUC_{control}$.

Objective

To evaluate the antioxidant activity by lipophylic and hydrophilic ORAC method of the following mixtures:

mixture 1 (consisting of samples 9617, 6714 and T3251 in the ratio 1:1:1)

mixture 2 (consisting of samples 2705, 940 and T3251 in the ratio 1:1:5).

Materials

AAPH and Trolox are from Sigma GmbH (Steinheim, Germany) and sodium fluorescein from Riedel-of-Haën (Seelze, Germany) and the others are analytical standard reagents.

Methodology

Hexane (1 mg/mL) was added in the individual samples, the samples were agitated during 3 minutes in vortex and centrifuged during two minutes in 700 g. The supernatant was removed, evaporated under nitrogen flow and analyzed as lipophylic portion. The soil body was analyzed as hydrophilic fraction.

The latter was solubilized in acetone:water (50% v/v), mixed in the ratio indicated for each one of the mixtures and appropriately diluted in 75 nM phosphate buffer pH 7.0. Thus, 25 μL of sample were added to 150 μL of 40 nM fluorescein solution (in 75 mM phosphate buffer pH 7.0) in plate of 96 wells. After incubation at 37° C. during 30 minutes, 25 μL of 153 mM AAPH solution was added (in 75 mM phosphate buffer pH 7.0) and the plate was stirred in high intensity during 10 seconds. The reading was made each minute for one hour with wave length of excitement 485/20 nm and emission 528/20 nm (reading of plates—Multi Detection microplate reader SynergyBIOTEK). The blank consisted of 200 μL of 75 mM phosphate buffer pH 7.0 and in the control the sample was replaced by 25 μL of 75 mM phosphate buffer pH 7.0.

The lipophylic portion was solubilized, mixed in the ratio indicated above for each mixture and diluted in acetone:water (50% v/v) having 7% of β-cyclodextrin randomly, methylated (RMCD). The analysis was performed as in the hydrophilic portion using the solution of RMCD as blank and controlled.

As a note, the mixture 2 was solubilized only in acetone and diluted in RMCD.

Results:

FIGS. 9 to 12 represent the correlations between the area difference on the curve of the samples in relation to the control (net AUC) and the concentration of the mixtures for hydrophilic and lipophylic evaluation.

The values of the antioxidant activities of the samples are presented below.

TABLE 6

Antioxidant activity of the samples.

| Sample | Activity (μmol eq Trolox/g of the sample) |
|---|---|
| Mixture 1 hydrophylic | 507 ± 53 |
| Mixture 1 lipophylic | 428 ± 7 |
| Mixture 2 hydrophylic | 190 ± 14 |
| Mixture 2 lipophylic | 1087 ± 89 |

The analyzed samples presented total antioxidant activity comparative considerable compared with Trolox® (400 μmol/g), the lipophylic portion being in mixture 2 the majority component of the activity.

Application And Stability Studies

The application of the active ingredients had been carried out on bases of Chronos (BDP. 581.9870.2 and 581.9869.3) and Fotoequilíbrio FPS 30 (581.9868.2) in the first phase. In this stage of individual evaluation of the active ingredients, the stability was carried out according to REVE protocol for green tea and cacao, since the other active ingredients already had history of application in end product. A more significant color modification in temperature conditions of 37° C. and 45° C. for FPS 30 was observed with green tea. However, it is pointed out that this raw material was applied in a concentration of 0.1%, 100× superior to the indicated final concentration (0.001%). The other characteristics in the other products and conditions had not suffered significant alterations.

In the second phase, already with the defined mixture (in accordance with the tests presented above), it was performed the application of the mixture of green tea (0.001%), tocopherol (0.001%) and cacao (0.001%) in the bases of Fotoequilíbrio FPS 30 and Chronos FPS 15, according to REVE protocol. During 30 days no significant change was detected.

Data:

TABLE 7

Codes and status (GSP/CMP)
New antioxidant complex

| Raw material | BDP | GSP | CMP |
|---|---|---|---|
| *Cacao* extract | 6714 | Definitive | Approved |
| Green Tea extract | 9617 | Definitive | Definitive |
| Tocopherol acetate | 1213 | Definitive | Definitive |

Tocopherol

All the tests presented had been carried out with the alpha-tocopherol. The proposed end products, however, use tocopherol acetate, which cannot be evaluated in vitro as it depends on the specific enzyme presence (estearases) that is present in the skin.

In view of this, an extensive search in literature on data of tocopherol acetate conversion into in tocopherol was performed. In this search various bioconversion data which range from 5% to 100% had been found. For the purposes of this evaluation it was, then, decided to use the worse case described in literature (bioconversion rate of 5%) to guarantee that the added acetate will be available in the concentration wherein the tests had been carried out. Thus, the rule of conversion of the amount of tocopherol to acetate was established as being a concentration 20× higher of the latter that shall be added to the end formulation.

The invention claimed is:

1. An antioxidant complex having a synergistic antioxidant effect consisting essentially of:

a) from 1 µg/ml to 20000 µg/ml of Vitamin E;
b) from 10 µg/ml to 1000 µg/ml of green tea extract; and
c) from 10 µg/ml to 1000 µg/ml of *Theobroma cacao* extract,
wherein all the amounts are based on the total weight of the antioxidant complex.

2. The antioxidant complex according to claim 1, wherein
a) the amount of Vitamin E is from 10 µg/ml to 200 µg/ml;
b) the amount of green tree extract is from 10 µg/ml to 100 µg/ml; and
c) the amount of *Theobroma cacao* extract is from 10 µg/ml to 100 µg/ml,
wherein all the amounts are based on the total weight of the antioxidant complex.

3. The antioxidant complex according to claim 1, wherein said Vitamin E is tocopherol or tocopherol acetate.

4. The antioxidant complex according to claim 1, wherein said green tea extract is a mixture of polyphenols, including catechins.

5. The antioxidant complex according to claim 1, wherein said *Theobroma cacao* extract is rich in catechins and xanthines.

6. The antioxidant complex according to claim 1, wherein
a) the Vitamin E is tocopherol acetate which is present in an amount of 10 µg/ml;
b) the green tea extract is a mixture of polyphenols, including catechins, and the green tea extract is present in an amount of 10 µg/ml; and
c) the *Theobroma cacao* extract is rich in catechins and xanthines, and the *Theobroma cacao* extract is present in amount of 10 µg/ml,
wherein all the amounts are based on the total weight of the antioxidant complex.

7. An antioxidant complex having a synergistic antioxidant effect consisting essentially of
a) from 1 µg/ml to 20000 µg/ml of Vitamin E;
b) from 10 µg/ml to 1000 µg/ml of green tea extract; and
c) from 10 µg/ml to 1000 µg/ml of *Theobroma cacao* extract, wherein all the amounts are based on the total weight of the antioxidant complex, and at least one additional antioxidant selected from the group consisting of butylated hydroxytoluene (BHT), butylated hydroxyanisole (BHA), and tert-butylhydroguinone (TBHQ).

8. A cosmetic composition consisting essentially of the antioxidant complex of claim 1; and a cosmetically acceptable carrier.

9. The cosmetic composition according to claim 8, wherein the amount of antioxidant complex ranges from 0.003% to 3.000% by weight, based on the total weight of the composition.

10. A pharmaceutical composition consisting essentially of:
a) the antioxidant complex of claim 1; and
b) a pharmaceutically acceptable carrier.

11. The pharmaceutical composition according to claim 10, wherein the amount of antioxidant complex ranges from 0.003% to 3.000% by weight, based on the total weight of the composition.

12. A method of manufacturing a cosmetic composition consisting essentially of the steps of:
forming a cosmetic composition consisting essentially of the antioxidant composition of claim 1, wherein said cosmetic composition combats molecular and morphological damages from lipoperoxidation, DNA oxidation and protein oxidation reactions, combating skin aging, combating damages caused by the sun and by adverse conditions including pollution, stress, and wind.

13. A method of manufacturing a pharmaceutical composition consisting essentially of the steps of:
forming a pharmaceutical composition consisting essentially of the antioxidant composition of claim 1, wherein said pharmaceutical composition combats molecular and morphological damages from lipoperoxidation, DNA oxidation and protein oxidation reactions, combating skin aging, combating damages caused by the sun and by adverse conditions including pollution, stress, and wind.

14. A method for treating cell and skin damage consisting essentially of treating a patient in need thereof with a cosmetic composition comprising the antioxidant complex of claim 1.

15. The method of claim 14, wherein the cell or skin damage is associated with one or more of molecular and morphological damages from lipoperoxidation, DNA oxidation and protein oxidation reactions, combating skin aging, combating damages caused by the sun and by adverse conditions such as pollution, stress, and wind exposure.

* * * * *

UNITED STATES PATENT AND TRADEMARK OFFICE
CERTIFICATE OF CORRECTION

PATENT NO. : 8,383,168 B2
APPLICATION NO. : 13/126352
DATED : February 26, 2013
INVENTOR(S) : Da Lúz Moreira et al.

Page 1 of 1

It is certified that error appears in the above-identified patent and that said Letters Patent is hereby corrected as shown below:

In the Claims;

Column 21,
Line 39, "1000 µg/mlof *Theobroma cacao*" should read --1000 µg/ml of *Theobroma cacao*--.

Signed and Sealed this
Fourth Day of June, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,383,168 B2  Page 1 of 1
APPLICATION NO. : 13/126352
DATED : February 26, 2013
INVENTOR(S) : Da Lúz Moreira et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 50 days.

Signed and Sealed this
First Day of September, 2015

Michelle K. Lee
*Director of the United States Patent and Trademark Office*